US006997919B2

(12) United States Patent
Olsen et al.

(10) Patent No.: US 6,997,919 B2
(45) Date of Patent: Feb. 14, 2006

(54) IMPLANTABLE MEDICAL CONNECTOR FOR MEDICAL TUBING WITH ANCHORING FEATURES

(75) Inventors: James M. Olsen, Plymouth, MN (US); Michael Thomas Hegland, Mounds Views, MN (US)

(73) Assignee: Medtronic, Inc., Minneapolis, MN (US)

( * ) Notice: Subject to any disclaimer, the term of this patent is extended or adjusted under 35 U.S.C. 154(b) by 303 days.

(21) Appl. No.: 10/127,853

(22) Filed: Apr. 23, 2002

(65) Prior Publication Data

US 2003/0199853 A1    Oct. 23, 2003

(51) Int. Cl.
  *A61M 25/16*    (2006.01)
(52) U.S. Cl. .................................................. 604/535
(58) Field of Classification Search ........... 604/164.07, 604/905, 523, 533–538, 165.01, 243, 240, 604/264; 285/114–116, 328, 330, 381.1, 285/921
See application file for complete search history.

(56) References Cited

U.S. PATENT DOCUMENTS

| 3,683,926 | A | | 8/1972 | Suzuki | |
| 3,730,564 | A | * | 5/1973 | Bachle et al. | ............... 285/115 |
| 4,214,586 | A | | 7/1980 | Mericle | |

(Continued)

FOREIGN PATENT DOCUMENTS

AU              431177          12/1972

(Continued)

OTHER PUBLICATIONS

AccuRX Constant Flow Implantable Pump, ANS Life Gets Better, (pp. 1-5).

(Continued)

*Primary Examiner*—Nicholas D. Lucchesi
*Assistant Examiner*—Matthew F. DeSanto
(74) *Attorney, Agent, or Firm*—Banner & Witcoff, Ltd

(57) ABSTRACT

A connector and method of medical tubing is disclosed. The connector defines a fluid passageway, and the connector includes a first end, a first intermediate portion, a middle portion, a second intermediate portion, and a second end. The middle portion is located between the first intermediate portion and the second intermediate portion, and the first end is adapted to fit inside a proximal connector-receiving portion, and the second end is adapted to fit inside a distal connector-receiving portion. The connector includes at least a first protrusion and a second protrusion projecting from the connector, wherein a first protrusion is located between the first end and the first intermediate portion, and the second protrusion is located between the second intermediate portion and the second end. The connector includes a first tubular strain relief having an extending first portion that extends past the first end of the connector and is adapted to fit over a proximal connection section, and a second tubular strain relief having an extending second portion that extends past the second end of the connector and is adapted to fit over a distal connection section. When the first end of the connector is inserted into a proximal connector-receiving portion a first interlock fit is formed therebetween, and when the second end of the connector is inserted into the distal connector-receiving portion a second interlock fit is formed therebetween, resulting in a fluid tight connection between the proximal connector-receiving portion and the distal connector-receiving portion, and wherein at least the middle portion of the connector is exposed. The middle portion of the connector can include a suture receiving section that can be sutured to tissue of patient.

43 Claims, 2 Drawing Sheets

U.S. PATENT DOCUMENTS

| | | | |
|---|---|---|---|
| 4,230,109 A | 10/1980 | Geiss | |
| 4,265,428 A | 5/1981 | Rosemeier et al. | |
| 4,313,628 A * | 2/1982 | Duenke | 285/115 |
| 4,537,183 A | 8/1985 | Fogarty | |
| 4,547,194 A | 10/1985 | Moorehead | |
| 4,641,860 A | 2/1987 | McMickle et al. | |
| 4,672,979 A | 6/1987 | Pohndorf | |
| 4,683,895 A | 8/1987 | Pohndord | |
| 4,842,592 A | 6/1989 | Caggiani et al. | |
| 4,917,103 A | 4/1990 | Gambale et al. | |
| 5,007,435 A * | 4/1991 | Doan et al. | 607/119 |
| 5,036,862 A | 8/1991 | Pohndorf | |
| 5,053,015 A | 10/1991 | Gross | |
| 5,107,856 A | 4/1992 | Kristiansen et al. | |
| 5,129,891 A | 7/1992 | Young | |
| 5,152,298 A | 10/1992 | Kreyenhagen et al. | |
| 5,178,612 A | 1/1993 | Fenton, Jr. | |
| 5,190,529 A | 3/1993 | McCrory et al. | |
| 5,226,898 A * | 7/1993 | Gross | 604/243 |
| 5,242,431 A | 9/1993 | Kristiansen | |
| 5,273,053 A | 12/1993 | Pohndorf | |
| 5,312,337 A | 5/1994 | Flaherty et al. | |
| 5,360,418 A | 11/1994 | Weilbacher et al. | |
| 5,365,944 A | 11/1994 | Gambale | |
| 5,376,108 A | 12/1994 | Collins et al. | |
| 5,405,339 A * | 4/1995 | Kohnen et al. | 604/535 |
| 5,423,763 A | 6/1995 | Helland et al. | |
| 5,562,618 A | 10/1996 | Cai et al. | |
| 5,584,874 A | 12/1996 | Rugland et al. | |
| 5,613,945 A | 3/1997 | Cai et al. | |
| 5,628,780 A | 5/1997 | Helland et al. | |
| 5,632,729 A | 5/1997 | Cai et al. | |
| 5,637,102 A * | 6/1997 | Tolkoff et al. | 604/536 |
| 5,743,873 A | 4/1998 | Cai et al. | |
| 5,746,722 A | 5/1998 | Pohndorf et al. | |
| 5,824,032 A | 10/1998 | Belden | |
| 5,961,485 A | 10/1999 | Martin | |
| 5,984,711 A | 11/1999 | Woodard | |
| 6,013,051 A | 1/2000 | Nelson | |
| 6,099,519 A | 8/2000 | Olsen et al. | |
| 6,190,372 B1 | 2/2001 | Racz | |
| 6,238,369 B1 | 5/2001 | Burbank et al. | |
| 6,254,589 B1 | 7/2001 | Raoz | |

FOREIGN PATENT DOCUMENTS

| | | | |
|---|---|---|---|
| DE | 29709252 U1 | | 8/1997 |
| DE | 29709252 U1 | * | 9/1997 |

OTHER PUBLICATIONS

DuraCath Intrsspinal Catheters, ANS Life Gets Better (pp. 1-2).

Medtronic InDura Intrathecal Catheters (p. 1, front and back).

* cited by examiner

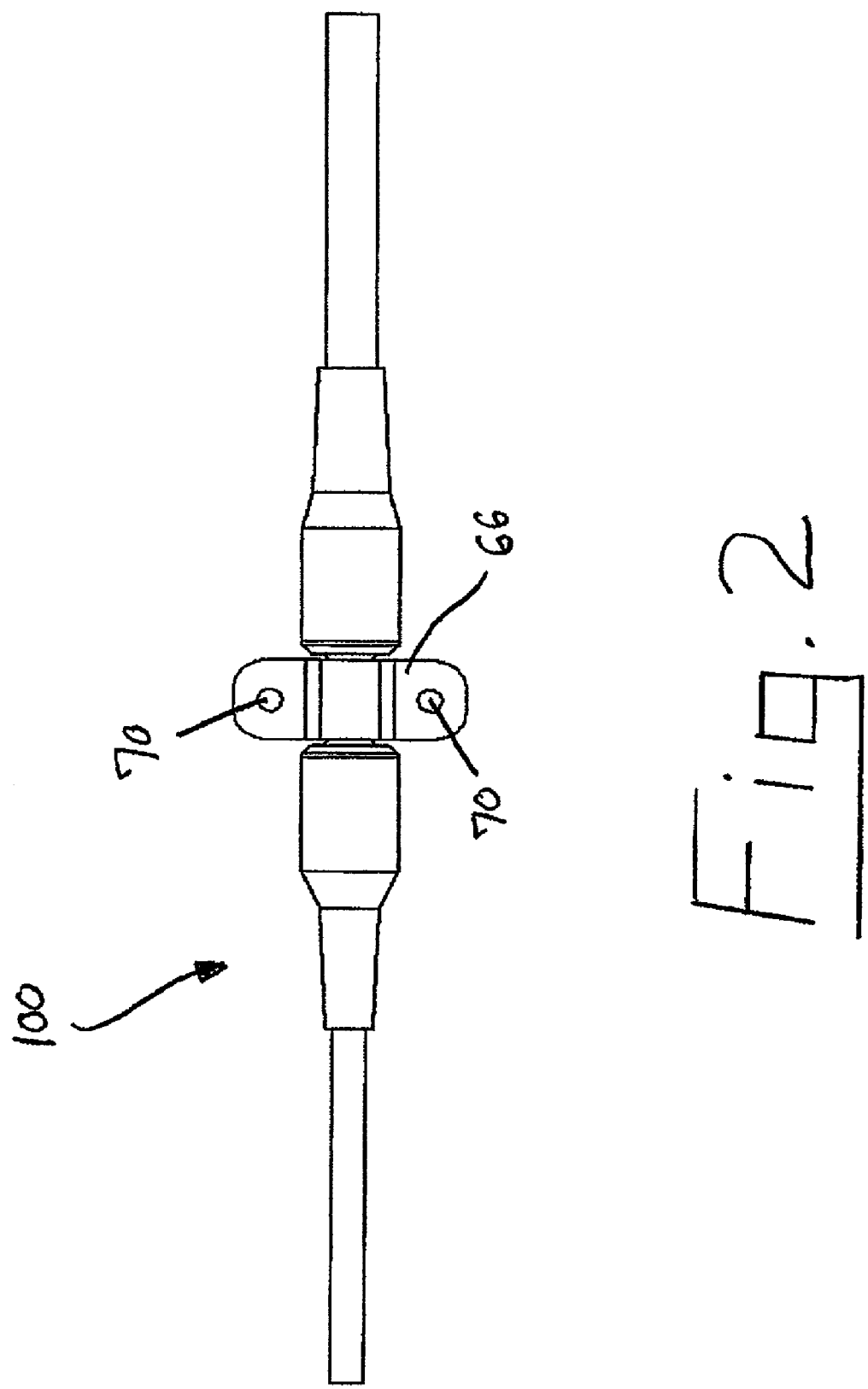

IMPLANTABLE MEDICAL CONNECTOR FOR MEDICAL TUBING WITH ANCHORING FEATURES

RELATED APPLICATION

Not applicable.

FIELD OF THE INVENTION

This invention relates to medical device connectors used for connecting medical tubing. More particularly, the invention is directed to a medical connector for connecting sections of a catheter.

BACKGROUND OF THE INVENTION

In numerous medical applications it becomes necessary to connect one section of tubing to another. In such situations it is important that the connection be secure so that it will not pull apart and that there be no leakage of fluid at the site of the connection. This is especially critical in applications where the tubing sections are implanted in the human body.

U.S. Pat. No. 5,405,339, which is incorporated herein by reference, teaches connector for connecting sections of medical tubing and a method for using the connector. The connector has an enlarged middle portion between first and second end portions. The end portions have a smaller diameter than the enlarged middle portion and are adapted to be inserted into the ends of the medical tubing sections. The connector can be grasped at the enlarged middle portion, thus simplifying the process of inserting the end portions into the tubing sections. Additionally, the opposing edges of the enlarged middle portion act as tubing stop surfaces that provide a positive indication that the connector is properly aligned.

While the invention described in U.S. Pat. No. 5,405,339 has solved numerous difficulties in the manufacture and use of the prior art medical devices, there is still certain areas for further improvement. For example, FIG. 3 of U.S. Pat. No. 5,405,339 teaches an addition of a circumferential suture groove in the surface of the enlarged middle portion that can only be used as a place at which the catheter may be anchored by suturing it to surrounding tissue if the connector is used without a strain relief. Col. 5, lines 37–43.

It would be desirable to provide a connector that provides a place at which the catheter may be anchored by suturing it to surrounding tissue, while at the same time providing a strain relief. It would also be desirable to provide a connector that provides stronger connections with greater useful life, and which is simple to use.

SUMMARY OF THE INVENTION

In accordance with the present invention there is disclosed an implantable medical device comprising a connector for connecting sections of medical tubing and a method for using the connector. The connector is shaped in a manner that solves the problems associated with prior art connectors and methods of connecting medical tubing.

More specifically, the present invention comprises a connector for medical tubing, the connector defining a fluid passageway, the connector having a first end, a first intermediate portion, a middle portion, a second intermediate portion, and a second end. The middle portion located between the first intermediate portion and the second intermediate portion. The end is adapted to fit inside a proximal connector-receiving portion of a proximal medical tube, the second end is adapted to fit inside a distal connector-receiving portion of a distal medical tube. The connector also has a least a first protrusion and a second protrusion projecting from the connector, wherein a first protrusion is located between the first end and the first intermediate portion, and the second protrusion is located between the second intermediate portion and the second end. The connector also includes a first tubular strain relief having an extending first portion that extends past the first end of the connector and is adapted to fit over a proximal connection section of a proximal medical tube, and a second tubular strain relief having an extending second portion that extends past the second end of the connector is and adapted to fit over a distal connection section of a distal medical tube. When the first end of the connector is inserted into the proximal connector-receiving portion a first interlock fit is formed therebetween, and when the second end of the connector is inserted into the distal connector-receiving portion a second interlock fit is formed therebetween. The result is a fluid tight connection between the proximal connector-receiving portion and the distal connector-receiving portion, and wherein at least the middle portion of the connector is exposed. In one embodiment, the first intermediate portion can include a first lip, and the second intermediate portion can include a second lip. Thus, when the first tubular strain relief fits over the first lip of the first intermediate portion, a third interlock fit is formed therebetween. Further, when the second tubular strain relief fits over the second lip of the second intermediate portion, a fourth interlock fit is formed therebetween.

In one embodiment, the middle portion further comprises a suture receiving portion. The suture receiving portion has a suitable structure that can be anchored by suturing to surrounding tissue or fascia of a patient. For example, but not by way of limitation, the suture receiving structure can have a suture receiving groove or hole. Preferably, the suture receiving portion has at least two locations to receive sutures so as to reduce rotation of the connector.

In one embodiment, the extending first portion of the first tubular strain relief is more flexible than a remainder of the first tubular strain relief and/or the extending second portion of the second tubular strain relief is more flexible than a remainder of the second tubular strain relief.

In one embodiment, the extending first portion of the first tubular strain relief tapers to a smaller outside diameter as it extends away from the first end of the connector and/or the extending second portion of the second tubular strain relief tapers to a smaller outside diameter as it extends away from the second end of the connector.

In one embodiment, at least the first intermediate portion of the connector is exposed and/or at least the second intermediate portion of the connector is exposed. Thus, the first intermediate portion and/or the second intermediate portion of the connector can be used as a convenient place to anchor the catheter to the tissue or fascia of a patient.

In one embodiment, the connector comprises a metal or metal alloy.

In one embodiment, the first tubular strain relief fits over the proximal connection section and a proximal fit is formed therebetween.

In one embodiment, the second tubular strain relief fits over the distal connection section and a distal fit is formed therebetween.

In one embodiment, the middle portion comprises a suture receiving portion. The suture receiving portion has a suitable structure that can be anchored to the tissue or fascia of a patient. For example, but not by way of limitation, the suture receiving structure can have a suture receiving groove or hole. Preferably, the suture receiving portion has at least two locations to receive sutures so as to reduce rotation of the connector.

In one embodiment, the present invention includes an implantable medical device comprising a proximal catheter having a proximal connection section, the proximal connection section having a proximal connector-receiving portion, and a distal catheter having a distal connection section, the distal connection section having a distal connector-receiving portion. The implantable medical device also has a connector between the proximal catheter and the distal catheter, the connector defining a fluid passageway, the connector having a first end, a first intermediate portion, a middle portion, a second intermediate portion, and a second end. The middle portion is located between the first intermediate portion and the second intermediate portion. The first end is adapted to fit inside the proximal connector-receiving portion, the second end is adapted to fit inside the distal connector-receiving portion. There is also at least a first protrusion and a second protrusion projecting from the connector, wherein the at least first protrusion is located between the first end and the first intermediate portion, and the second protrusion is located between the second intermediate portion and the second end. The invention further has a first tubular strain relief having an extending first portion that extends past the first end of the connector and fits over the proximal connection section, and a second tubular strain relief having an extending second portion that extends past the second end of the connector and fits over the distal connection section. Thus, when the first end of the connector is inserted into the proximal connector-receiving portion a first interlock fit is formed therebetween, and when the second end of the connector is inserted into the distal connector-receiving portion a second interlock fit is formed therebetween. The result is a fluid tight connection between the proximal catheter and the distal catheter, and wherein at least the middle portion of the connector is exposed. Since the middle portion of the connector is exposed, it can be anchored by suturing to surrounding tissue or fascia of a patient. The connector of this embodiment can have any or all combination of additional features recited in the preceding paragraphs.

BRIEF DESCRIPTION OF THE DRAWINGS

FIG. 2 is a side view of an alternative embodiment of the implantable medical device of the present invention.

DETAILED DESCRIPTION OF THE PREFERRED EMBODIMENTS

Figure 1:
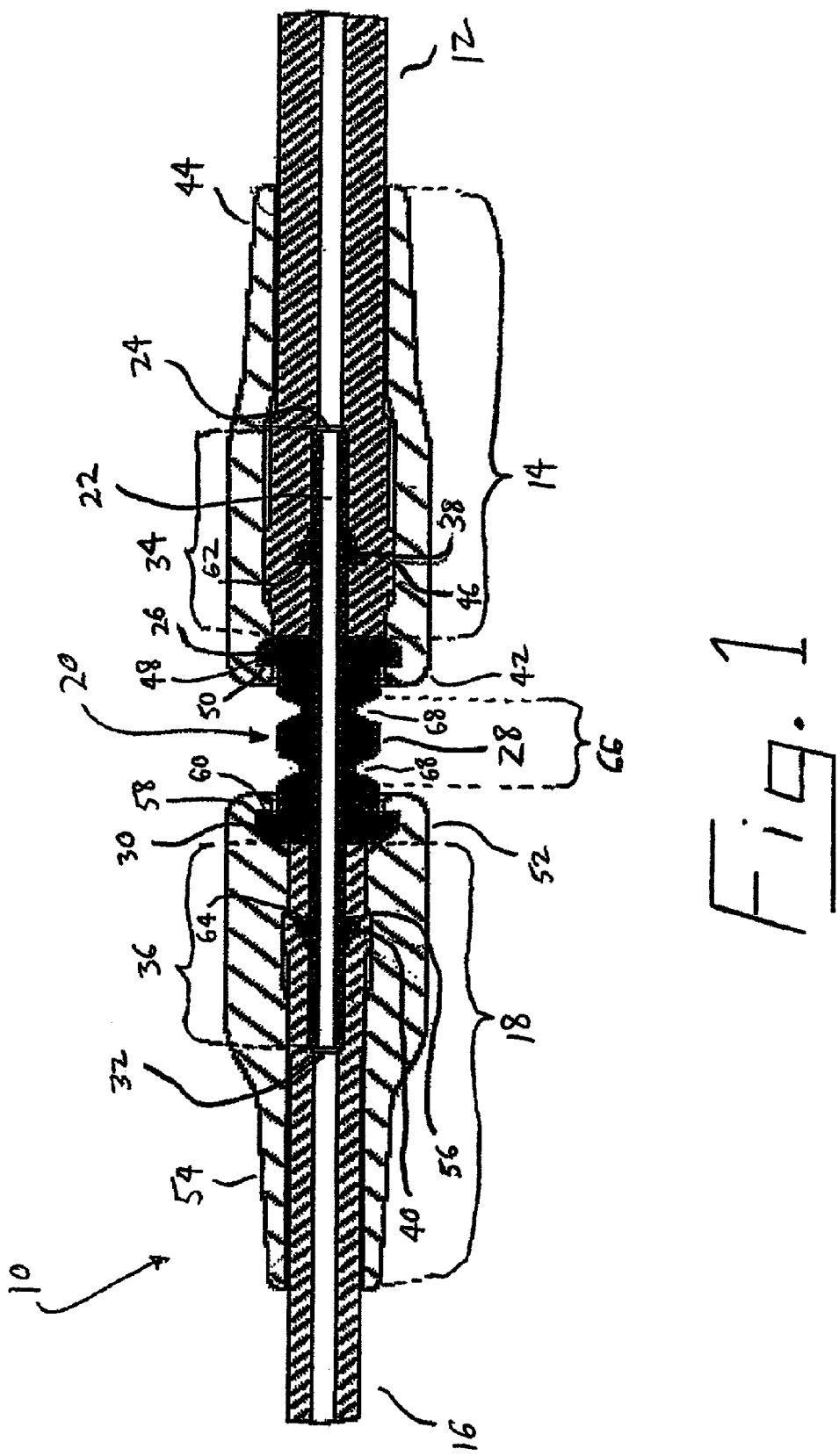
FIG. 1 is a side view of a implantable medical device in accordance with the present invention.

FIG. 1 is a side view of a implantable medical device used to connect sections of medical tubing in accordance with a preferred embodiment of the present invention. More specifically, as shown in FIG. 1, an implantable medical device 10 comprises a proximal catheter 12 having a proximal connection section 14, the proximal connection section 14 having a proximal connector-receiving portion 34. Implantable medical device 10 also has a distal catheter 16 having a distal connection section 18, the distal connection section 18 having a distal connector-receiving portion 36. Implantable medical device 10 also has a connector 20 between the proximal catheter 12 and the distal catheter 16, the connector 20 defining a fluid passageway 22, the connector 20 having a first end 24, a first intermediate portion 26, a middle portion 28, a second intermediate portion 30, and a second end 32. The middle portion 28 is located between the first intermediate portion 26 and the second intermediate portion 30. The first end 24 is adapted to fit inside the proximal connector-receiving portion 34, and the second end 32 is adapted to fit inside the distal connector-receiving portion 36.

Implantable medical device 10 has at least a first protrusion 38 and a second protrusion 40 projecting from the connector 20, wherein the first protrusion 38 is located between the first end 24 and the first intermediate portion 26, and the second protrusion 40 is located between the second intermediate portion 30 and the second end 32. Also provided is a first tubular strain relief 42 having an extending first portion 44 that extends past the first end 24 of the connector 20 and fits over the proximal connection section 14, and a second tubular strain relief 52 having an extending second portion 54 that extends past the second end 32 of the connector 20 and fits over the distal connection section 18. Thus, when the first end 24 of the connector 20 is inserted into the proximal connector-receiving portion 34 a first interlock fit 62 is formed therebetween. Also, when the second end 32 of the connector 20 is inserted into the distal connector-receiving portion 36 a second interlock fit 64 is formed therebetween, resulting in a fluid tight connection between the proximal catheter 12 and the distal catheter 16. As shown in FIG. 1, this construction results in at least the middle portion 28 of connector 20 being exposed. Because the middle portion 28 is exposed, the middle section 28 provides a convenient place at which the connector can be anchored by suturing it to surrounding tissue or fascia of a patient. As further shown in FIG. 1, the first intermediate portion 26 can include a first lip 48, and the second intermediate portion 30 can include a second lip 58. Thus, when the first tubular strain relief 42 fits over the first lip 48 of the first intermediate portion 26, a third interlock fit 50 is formed therebetween. Further, when the second tubular strain relief 52 fits over the second lip 58 of the second intermediate portion 30, a fourth interlock fit 60 is formed therebetween.

Preferably, the extending first portion 44 of the first tubular strain relief 42 is more flexible than a remainder of the first tubular strain relief 42, and the extending second portion 54 of the second tubular strain relief 52 is more flexible than a remainder of the second tubular strain relief 52. The difference in flexibility can be obtained in any suitable manner, including but not limited to a tapering of the first and second tubular stain reliefs as they extend away from the connector 20. Alternatively, different materials, or slits and/or holes defined in the first and second tubular strain reliefs can provide the desired difference in flexibility as will be recognized by those of skill in the art.

Preferably, the extending first portion 44 of the first tubular strain relief 42 tapers to a smaller outside diameter as it extends away from the first end 24 of the connector 20, and the extending second portion 54 of the second tubular strain relief 52 tapers to a smaller outside diameter as it extends away from the second end 32 of the connector 20.

In one embodiment, the first intermediate portion 26 and/or the second intermediate portion 30 have at least one portion that is exposed along with the middle portion 28. Thus, portions 26, 28 and/or 30 can define at least two grooves 68 at which the connector 20 can be anchored by suturing it to the tissue or fascia of a patient. By providing at least two places for suturing, connector 20 provides a structure that can be sutured to the tissue or fascia of a patient that will not be a susceptible to rotation as a connector that has only one place to suture it to the tissue or fascia of a patient.

In a preferred embodiment, the connector 20 comprises a metal or metal alloy. Those of skill in the art will recognize that a metal or metal alloy can be sutured to the tissue or fascia of a patient more securely than a softer material, such as the material used for strain reliefs or for catheter tubing.

As shown in FIG. 1, when the first tubular strain relief 42 fits over the proximal connection section 14, a proximal fit 46 is formed therebetween. As also shown in FIG. 1, when the second tubular strain relief 52 fits over the distal connection section 18, a distal fit 56 is formed therebetween.

As shown in FIG. 1, the middle portion 28 further comprises a suture receiving portion 66. The suture receiving portion 66 has a suitable structure that can be anchored to the tissue or fascia of a patient. For example, but not by way of limitation, the suture receiving portion 66 can define a suture receiving groove 68 or hole 70. Preferably, the suture receiving portion 66 has at least two locations, e.g., at least two suture receiving grooves 68 or holes 70 to receive sutures so as to reduce rotation of the connector. As shown in FIG. 1, the suture receiving portion 66 defines two suture receiving grooves 68.

An alternative embodiment is shown in FIG. 2. In FIG. 2, device 100 is the same as the device 10 shown in FIG. 1, except that suture receiving portion 66 defines two holes 70 instead of two suture receiving grooves.

The present invention also provides a method for connecting implantable medical tubing. More specifically, the present invention comprises the step of providing a implantable medical device 10 comprising a proximal connection section 14, the proximal connection section 14 having a proximal connector-receiving portion 34; a distal connection section 18, the distal connection section 18 having a distal connector-receiving portion 36; a connector 20 between the proximal catheter 12 and the distal catheter 16, the connector 20 defining a fluid passageway 22, the connector 20 having a first end 24, a first intermediate portion 26, a middle portion 28, a second intermediate portion 30, and a second end 32, the middle portion 28 located between the first intermediate portion 26 and the second intermediate portion 30, the first end 24 adapted to fit inside the proximal connector-receiving portion 34, the second end 32 adapted to fit inside the distal connector-receiving portion 36, and at least a first protrusion 38 and a second protrusion 40 projecting from the connector 20, wherein a first protrusion 38 is located between the first end 24 and the first intermediate portion 26, and the second protrusion 40 is located between the second intermediate portion 30 and the second end 32; a first tubular strain relief 42 having an extending first portion 44 that extends past the first end 24 of the connector 20 and fits over the proximal connection section 14; and a second tubular strain relief 52 having an extending second portion 54 that extends past the second end 32 of the connector 20 and fits over the distal connection section 18.

A preferred method of the present invention further comprises the steps of placing the proximal connection section 14 over the first end 24 of the connector; inserting the first end 24 of the connector 20 into the proximal connector-receiving portion 34 to form a first interlock fit 62 therebetween; placing the distal connection section 18 over the second end 32 of the connector 20; inserting the second end 32 of the connector 20 into the distal connector-receiving portion 36 to form a second interlock fit 64 therebetween; thereby forming a fluid tight connection between the proximal connection section 14 and the distal connection section 18, and wherein at least the middle portion 28 of the connector 20 is exposed.

A preferred method further comprises the steps of providing the first intermediate portion 26 with a first lip 48, and the second intermediate portion 30 with a second lip 58. Thus, when the first tubular strain relief 42 is placed over the first lip 48 of the first intermediate portion 26, a third interlock fit 50 is formed therebetween. Further, when the second tubular strain relief 52 is placed over the second lip 58 of the second intermediate portion 30, a fourth interlock fit 60 is formed therebetween.

A preferred method farther comprises the steps of providing at least one suture receiving portion 66 on the middle portion 28 and anchoring the connector 20 by suturing the suture receiving portion 66 to tissue of a patient. In one embodiment, the method further comprises the steps of providing at least two suture receiving grooves 68 on the suture receiving portion 66 and anchoring the connector 20 by suturing the suture receiving grooves 68 to tissue of a patient. In one embodiment, the method further comprises the steps of providing at least two suture receiving holes 70 on the suture receiving portion 66 and anchoring the connector 20 by suturing the suture receiving holes 70 to tissue of a patient.

From the foregoing detailed description of specific embodiments of the invention, it should be apparent that a medical connector and method for its use has been disclosed. Although particular embodiments of the invention have been disclosed herein in detail, this has been done for the purpose of illustration only, and is not intended to be limiting with respect to the scope of the appended claims, which follow. In particular, it is contemplated by the inventors that various substitutions, alterations and modifications may be made to the embodiments of the invention without departing from the spirit and scope of the invention as defined by the claims. Further, although the embodiments disclosed relate primarily to use of the connector for connecting catheter sections, the connector could be used for other applications where it is desirable to connect separate sections of medical tubing together, especially those situations where the tubing is to be implanted in the human body. Such applications include connecting sections of stents, penile implants and sphincter implants.

We claim:

1. An implantable medical connector (20) for medical tubing, the connector (20) comprising:

a connector body comprising a first end (24), a first intermediate portion (26), a middle portion (28), a second intermediate portion (30), and a second end (32), the middle portion (28) located between the first intermediate portion (26) and the second intermediate portion (30), the first end (24) adapted to fit inside a proximal connector-receiving portion, the second end (32) adapted to fit inside a distal connector-receiving portion, and at least a first protrusion (38) and a second protrusion (40) projecting from the connector body, wherein a first protrusion (38) is located between the first end (24) and the first intermediate portion (26), and the second protrusion (40) is located between the second intermediate portion (30) and the second end (32), the connector body defining a fluid passageway (22);

a first tubular strain relief (42) having an extending first portion (44) that extends past the first end (24) of the connector body and adapted to fit over a proximal connection section, the first tubular strain relief adapted to fit over a section of the first intermediate portion of the connector body to form a direct interlock fit therebetween; and a second tubular strain relief (52) having an extending second portion (54) that extends past the second end (32) of the connector body and adapted to fit over a distal connection section, the second tubular strain relief adapted to fit over a section of the second intermediate portion of the connector body to form a direct interlock fit therebetween, wherein when the first end (24) of the connector body is inserted into the proximal connector-receiving portion an interlock fit is formed therebetween, and wherein when the second end (32) of the connector body is inserted into the distal connector-receiving portion an interlock fit is formed therebetween, resulting in a fluid tight connection between the proximal connector-receiving portion and the distal connector-receiving portion, and wherein a surface of the middle portion (28) of the connector body is exposed.

2. The implantable medical connector (20) of claim 1, wherein the exposed surface of the middle portion (28) further comprises a suture receiving portion (66) for anchoring the connector (20) to tissue.

3. The implantable medical connector (20) of claim 2, wherein the suture receiving portion (66) defines at least one suture receiving groove (68).

4. The implantable medical connector (20) of claim 2, wherein the suture receiving portion (66) defines at least two suture receiving grooves (68).

5. The implantable medical connector (20) of claim 2, wherein the suture receiving portion (66) defines at least one suture receiving hole (70).

6. The implantable medical connector (20) of claim 2, wherein the suture receiving portion (66) defines at least two suture receiving holes (70).

7. The implantable medical connector (20) of claim 1, wherein the extending first portion (44) of the first tubular strain relief (42) is more flexible than a remainder of the first tubular strain relief (42).

8. The implantable medical connector (20) of claim 1, wherein the extending second portion (54) of the second tubular strain relief (52) is more flexible than a remainder of the second tubular strain relief (52).

9. The implantable medical connector (20) of claim 1, wherein the extending first portion (44) of the first tabular strain relief (42) is more flexible than a remainder of the first tubular strain relief (42), and the extending second portion (54) of the second tubular strain relief (52) is more flexible than a remainder of the second tubular swain relief (52).

10. The implantable medical connector (20) of claim 1, wherein the extending first portion (44) of the first tubular strain relief (42) tapers to a smaller outside diameter as it extends away from the first end (24) of the connector (20).

11. The implantable medical connector (20) of claim 1, wherein the extending second portion (54) of the second tubular strain relief (52) tapers to a smaller outside diameter as it extends away from the second end (32) of the connector (20).

12. The implantable medical connector (20) of claim 1, wherein the extending first portion (44) of the first tubular strain relief (42) tapers to a smaller outside diameter as it extends away from the first end (24) of the connector (20), and the extending second portion (54) of the second tubular strain relief (52) tapers to a smaller outside diameter as it extends away from the second end (32) of the connector (20).

13. The implantable medical connector (20) of claim 1, wherein a surface of the first intermediate portion (26) of the connector (20) is exposed.

14. The implantable medical connector (20) of claim 1, wherein a surface of the second intermediate portion (30) of the connector (20) is exposed.

15. The implantable medical connector (20) of claim 1, wherein a surface of the first intermediate portion (26) and a surface of the second intermediate portion (30) of the connector (20) is exposed.

16. The implantable medical connector (20) of claim 1, wherein the connector (20) comprises a metal or metal alloy.

17. The implantable medical connector (20) of claim 1, wherein when the first tubular strain relief (42) fits over the proximal connection section (14) a proximal fit (46) is formed therebetween.

18. The implantable medical connector (20) of claim 1, wherein when the second tubular strain relief (52) fits over the distal connection section (18) a distal fit (56) is formed therebetween.

19. The implantable medical device (10) of claim 1, wherein a surface of the second intermediate portion (30) of the connector (20) is exposed.

20. The implantable medical device (10) of claim 1, wherein a surface of the first intermediate portion (26) and a surface of the second intermediate portion (30) of the connector (20) is exposed.

21. The implantable medical connector (20) of claim 1, wherein the first intermediate portion (26) includes a first lip (48), and the second intermediate portion (30) includes a second lip (58), wherein when the first tabular swain relief (42) fits over the first lip (48) of the first intermediate portion (26), an interlock fit (50) is formed therebetween, and when the second tubular strain relief (52) fits over the second lip (58) of the second intermediate portion (30), an interlock fit (60) is formed therebetween.

22. An implantable medical device (10) comprising:
    a proximal catheter (12) having a proximal connection section (14), the proximal connection section (14) having a proximal connector-receiving portion (34);
    a distal catheter (16) having a distal connection section (18), the distal connection section (18) having a distal connector-receiving portion (36);
    a connector body between the proximal catheter (12) and the distal catheter (16), the connector body defining a fluid passageway (22), the connector (20) having a first end (24), a first intermediate portion (26), a middle portion (28), a second intermediate portion (30), and a second end (32), the middle portion (28) located between the first intermediate portion (26), and the second intermediate portion (30), the first end (24) adapted to fit inside the proximal connector-receiving portion (34), the second end (32) adapted to fit inside the distal connector-receiving portion (36), and at least a first protrusion (38) and a second protrusion (40) projecting from the connector body, wherein a first protrusion (38) is located between the first end (24) and the first intermediate portion (26), and the second protrusion (40) is located between the second intermediate portion (30) and the second end (32);
    a first tubular swain relief (42) having an extending first portion (44) that extends past the first end (24) of the connector body and fits over the proximal connection section (14), the first tubular strain relief adapted to fit over a section of the first intermediate portion if the connector body to form a direct interlock fit therebetween; and a second tubular strain relief (52) having an extending second portion (54) that extends past the second end (32) of the connector body and fits over the distal connection section (18), the second tubular strain relief adapted to fit over a section of the second intermediate portion of the connector body to form a direct interlock fit therebetween, wherein when the first end (24) of the connector body is inserted into the proximal connector-receiving portion (34) an interlock fit (62) is formed therebetween, and wherein when the second end (32) of the connector (20) is inserted into the distal connector-receiving portion (36) an interlock fit (64) is formed therebetween, resulting in a fluid tight connection between the proximal catheter (12) and the distal catheter (16), and wherein a surface of the middle portion (28) of the connector (20) is exposed.

23. The implantable medical device (10) of claim 22, wherein the exposed surface of the middle portion (28) further comprises a suture receiving portion (66) for anchoring the connector (20) to tissue.

24. The implantable medical device (10) of claim 23, wherein the suture receiving portion (66) defines at least one suture receiving groove (68).

25. The implantable medical device (10) of claim 23, wherein the suture receiving portion (66) defines at least two suture receiving grooves (68).

26. The implantable medical device (10) of claim 23, wherein the suture receiving portion (66) defines at least one suture receiving hole (70).

27. The implantable medical device (10) of claim 23, wherein the suture receiving portion (66) defines at least two suture receiving holes (70).

28. The implantable medical device (10) of claim 22, wherein the extending first portion of the first tubular strain relief is more flexible than a remainder of the first tubular strain relief.

29. The implantable medical device (10) of claim 22, wherein the extending second portion of the second tubular strain relief is more flexible than a remainder of the second tubular strain relief.

30. The implantable medical device (10) of claim 22, wherein the extending first portion of the first tubular strain relief is more flexible than a remainder of the first tubular strain relief, and the extending second portion of the second tubular strain relief is more flexible than a remainder of the second tubular strain relief.

31. The implantable medical device (10) of claim 22, wherein the extending first portion of the first tubular strain relief tapers to a smaller outside diameter as it extends away from the first end (24) of the connector (20).

32. The implantable medical device (10) of claim 22, wherein the extending second portion of the second tubular strain relief tapers to a smaller outside diameter as it extends away from the second end (32) of the connector (20).

33. The implantable medical device (10) of claim 22, wherein the extending first portion of the first tubular stain relief tapers to a smaller outside diameter as it extends away from the first end (24) of the connector (20), and the extending second portion of the second tubular strain relief tapers to a smaller outside diameter as it extends away from the second end (32) of the connector (20).

34. The implantable medical device (10) of claim 22, wherein a surface of the first intermediate portion (26) of the connector (20) is exposed.

35. The implantable medical device (10) of claim 22, wherein the connector comprises a metal or mental alloy.

36. The implantable medical device (10) of claim 22, wherein when the first tubular stain relief (42) fits over the proximal connection section (14) a proximal fit (46) is formed therebetween.

37. The implantable medical device (10) of claim 22, wherein when the second tubular strain relief (52) fits over the distal connection section (18) a distal fit (56) is formed therebetween.

38. The implantable medical device (10) of claim 22, wherein the first intermediate portion (26) includes a first lip (48), and the second intermediate portion (30) includes a second lip (58), wherein when the first tubular strain relief (42) fits over the first lip (48) of the first intermediate portion (26), an interlock fit (50) is formed therebetween, and when the second tubular strain relief (52) fits over the second lip (58) of the second intermediate portion (30), an interlock fit (60) is formed therebetween.

39. A method for connecting implantable medical tubing comprising:

providing a implantable medical device (10) comprising a proximal connection section (14), the proximal connection section (14) having a proximal connector-receiving portion (34); a distal connection section (18), the distal connection section (18) having a distal connector-receiving portion (36); a connector (20) between the proximal catheter (12) and the distal catheter (16), the connector (20) comprising a connector body and defining a fluid passageway (22), the connector body having a first end (24), a first intermediate portion (26), a middle portion (28), a second intermediate portion (30), and a second end (32), the middle portion (28) located between the first intermediate portion (26) and the second intermediate portion (30), the first end (24) adapted to fit inside the proximal connector-receiving portion (34), the second end (32) adapted to fit inside the distal connector-receiving portion (36), and at least a first protrusion (38) and a second protrusion (40) projecting from the connector body, wherein a first protrusion (38) is located between the first end (24) and the first intermediate portion (26), and the second protrusion (40) is located between the second intermediate portion (30) and the second end (32); a first tubular strain relief (42) having an extending first portion (44) that extends past the first end (24) of the connector body and fits over the proximal connection section (14), the first tubular strain relief adapted to fit over a section of the first intermediate portion of the connector body to form a direct interlock fit therebetween; and a second tubular strain relief (52) having an extending second portion (54) that extends past the second end (32) of the connector body and fits over the distal connection section (18), the second tubular strain relief adapted to fit over a section of the second intermediate portion of the connector body to form a direct interlock fit therebetween;

placing the proximal connection section (14) over the first end (24) of the connector body;

inserting the first end (24) of the connector (20) into the proximal connector-receiving portion (34) to form an interlock fit (62) therebetween;

placing the distal connection section (18) over the second end (32) of the connector body;

inserting the second end (32) of the connector body into the distal connector-receiving portion (36) to form an interlock fit (64) therebetween;

thereby forming a fluid tight connection between the proximal connection section (14) and the distal connection section (18), and wherein a surface of the middle portion (28) of the connector body is exposed.

40. The method of claim 39, further comprising the steps of providing at least one suture receiving portion (66) on the exposed surface of the middle portion (28) and anchoring the connector (20) by suturing the suture receiving portion (66) to tissue of a patient.

41. The method of claim 40, further comprising the steps of providing at least two suture receiving grooves (68) on the suture receiving portion (66) and anchoring the connector (20) by suturing the suture receiving grooves (68) to tissue of a patient.

42. The method of claim 40, further comprising the steps of providing at least two suture receiving holes (70) on the suture receiving portion (66) and anchoring the connector (20) by suturing the suture receiving holes (70) to tissue of a patient.

43. The method of claim 39, further comprising the steps of providing the first intermediate portion (26) with a first lip (48), and the second intermediate portion (30) wit a second lip (58), placing the first tubular strain relief (42) over the first lip (48) of the first intermediate portion (26) to form an interlock fit (50) therebetween, and placing the second tubular strain relief (52) over the second lip (58) of the second intermediate portion 30 to form an interlock fit (60) therebetween.

* * * * *

UNITED STATES PATENT AND TRADEMARK OFFICE
CERTIFICATE OF CORRECTION

PATENT NO.       : 6,997,919 B2
APPLICATION NO.  : 10/127853
DATED            : February 14, 2006
INVENTOR(S)      : James M. Olsen et al.

It is certified that error appears in the above-identified patent and that said Letters Patent is hereby corrected as shown below:

The title page should be deleted to appear as per attached title page.

The sheet of drawings consisting of figures 1-2 should be deleted to appear as per attached figures 1-2.

Signed and Sealed this

Fifteenth Day of August, 2006

JON W. DUDAS
*Director of the United States Patent and Trademark Office*

(12) United States Patent
Olsen et al.

(10) Patent No.: US 6,997,919 B2
(45) Date of Patent: Feb. 14, 2006

(54) IMPLANTABLE MEDICAL CONNECTOR FOR MEDICAL TUBING WITH ANCHORING FEATURES

(75) Inventors: James M. Olsen, Plymouth, MN (US); Michael Thomas Hegland, Mounds Views, MN (US)

(73) Assignee: Medtronic, Inc., Minneapolis, MN (US)

( * ) Notice: Subject to any disclaimer, the term of this patent is extended or adjusted under 35 U.S.C. 154(b) by 303 days.

(21) Appl. No.: 10/127,853

(22) Filed: Apr. 23, 2002

(65) Prior Publication Data
US 2003/0199853 A1 Oct. 23, 2003

(51) Int. Cl.
A61M 25/16 (2006.01)
(52) U.S. Cl. .................................. 604/535
(58) Field of Classification Search .......... 604/164.07, 604/905, 523, 533–538, 165.01, 243, 240, 604/264; 285/114–116, 328, 330, 381.1, 285/921
See application file for complete search history.

(56) References Cited

U.S. PATENT DOCUMENTS

| 3,683,926 A | 8/1972 | Suzuki | |
|---|---|---|---|
| 3,730,564 A | * | 5/1973 | Bachle et al. ............... 285/115 |
| 4,214,586 A | 7/1980 | Mericle | |

(Continued)

FOREIGN PATENT DOCUMENTS

AU 431177 12/1972

(Continued)

OTHER PUBLICATIONS

AccuRX Constant Flow Implantable Pump, ANS Life Gets Better, (pp. 1-5).

(Continued)

*Primary Examiner*—Nicholas D. Lucchesi
*Assistant Examiner*—Matthew F. DeSanto
(74) *Attorney, Agent, or Firm*—Banner & Witcoff, Ltd

(57) ABSTRACT

A connector and method of medical tubing is disclosed. The connector defines a fluid passageway, and the connector includes a first end, a first intermediate portion, a middle portion, a second intermediate portion, and a second end. The middle portion is located between the first intermediate portion and the second intermediate portion, and the first end is adapted to fit inside a proximal connector-receiving portion, and the second end is adapted to fit inside a distal connector-receiving portion. The connector includes at least a first protrusion and a second protrusion projecting from the connector, wherein a first protrusion is located between the first end and the first intermediate portion, and the second protrusion is located between the second intermediate portion and the second end. The connector includes a first tubular strain relief having an extending first portion that extends past the first end of the connector and is adapted to fit over a proximal connection section, and a second tubular strain relief having an extending second portion that extends past the second end of the connector and is adapted to fit over a distal connection section. When the first end of the connector is inserted into a proximal connector-receiving portion a first interlock fit is formed therebetween, and when the second end of the connector is inserted into the distal connector-receiving portion a second interlock fit is formed therebetween, resulting in a fluid tight connection between the proximal connector-receiving portion and the distal connector-receiving portion, and wherein at least the middle portion of the connector is exposed. The middle portion of the connector can include a suture receiving section that can be sutured to tissue of patient.

43 Claims, 2 Drawing Sheets

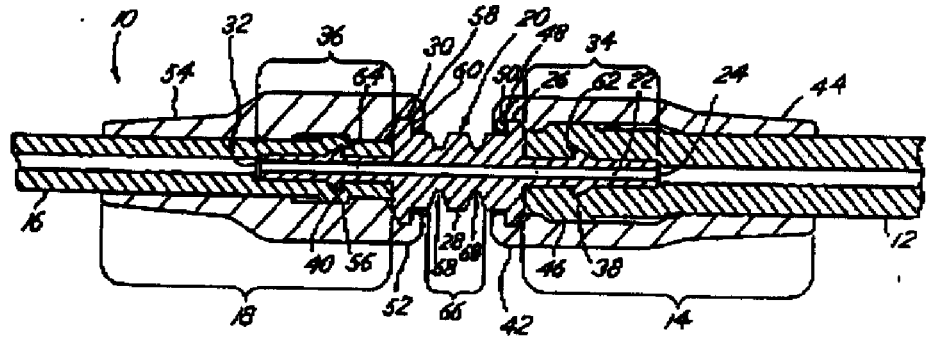

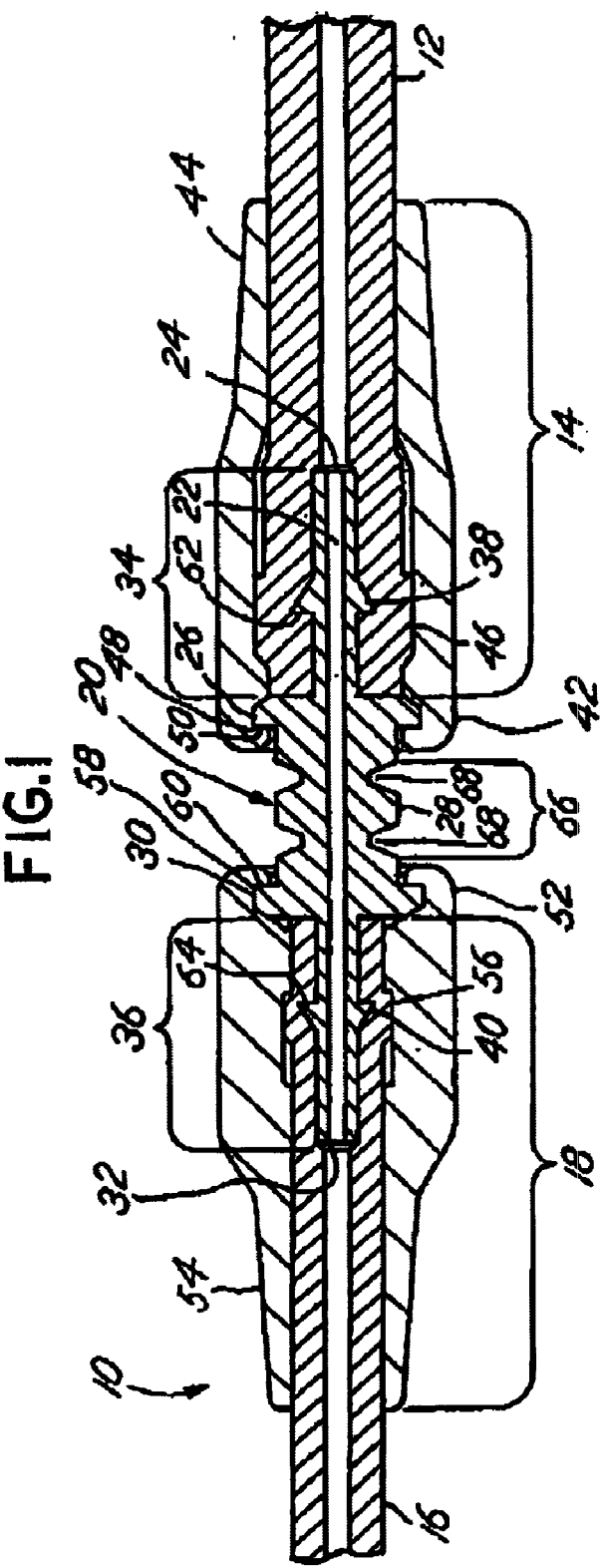
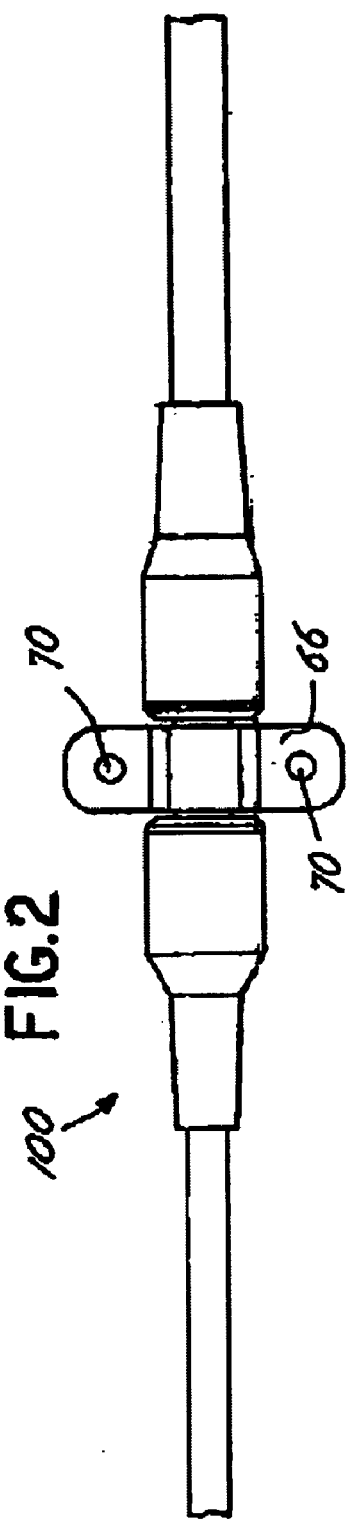
FIG.1
FIG.2

UNITED STATES PATENT AND TRADEMARK OFFICE
CERTIFICATE OF CORRECTION

PATENT NO.        : 6,997,919 B2
APPLICATION NO. : 10/127853
DATED             : February 14, 2006
INVENTOR(S)      : James M. Olsen et al.

It is certified that error appears in the above-identified patent and that said Letters Patent is hereby corrected as shown below:

Col. 7, Line 48: "first tabular" should read --first tubular--

Col. 7, Line 52: "swain relief" should read --strain relief--

Col. 8, Line 34: "tabular swain" should read --tubular strain--

Col. 8, Line 64: "tubular swain" should read --tubular strain--

Col. 9, Line 1:   "portion if" should read --portion of--

Col. 9, Line 62: "tubular stain" should read --tubular strain--

Col. 10, Line 5: "mental alloy" should read --metal alloy--

Col. 10, Line 7: "tubular stain" should read --tubular strain--

Col. 12, Line 10: "wit a second" should read --with a second--

Signed and Sealed this

Third Day of November, 2009

David J. Kappos
*Director of the United States Patent and Trademark Office*